Figure 1:
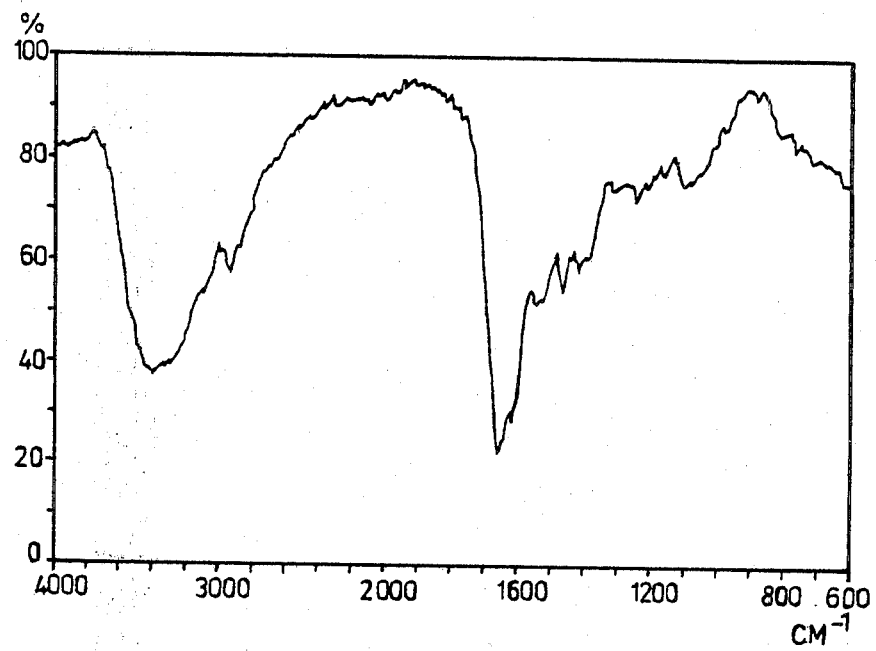

United States Patent [19]

Metzger et al.

[11] 4,416,870

[45] Nov. 22, 1983

[54] ANTIBIOTIC COMPOUND, ITS PRODUCTION AND ITS MEDICINAL USE

[75] Inventors: Karl G. Metzger; Jörg Pfitzner; Delf Schmidt, all of Wuppertal; Horst Weyland, Bremerhaven; Günter Benz, Velbert; Theo Schröder, Wuppertal, all of Fed. Rep. of Germany

[73] Assignee: Bayer Aktiengesellschaft, Leverkusen, Fed. Rep. of Germany

[21] Appl. No.: 340,418

[22] Filed: Jan. 18, 1982

[30] Foreign Application Priority Data

Jan. 23, 1981 [DE] Fed. Rep. of Germany ....... 3102136

[51] Int. Cl.³ .................. C07C 103/52; A61K 31/495

[52] U.S. Cl. .......................... 424/172; 260/112.5 R; 435/71

[58] Field of Search ................... 260/112.5 R; 424/172

Primary Examiner—Robert Gerstl
Attorney, Agent, or Firm—Sprung, Horn, Kramer & Woods

[57] ABSTRACT

The invention relates to an antibiotic compound which can be in the iron-free or iron-containing form and has the structural formula (A) as described herein. The compound possesses antimicrobial activity. Also included in the invention are fermentation processes for preparation of the above-mentioned antibiotic compound. In addition, the invention includes pharmaceutical compositions containing said antibiotic compound and the use of said antibiotic compound and compositions for combating bacterial infections.

10 Claims, 3 Drawing Figures

ANTIBIOTIC COMPOUND, ITS PRODUCTION AND ITS MEDICINAL USE

The present invention relates to a new antibiotic compound, to a microbiological process for its production from a Streptomyces strain and to its use as an antimicrobial agent in medicine.

It has already been disclosed that a number of compounds of microbial origin have antimicrobial actions. Some of these antibiotics are not completely satisfactory in their spectra of action. They frequently have still further disadvantages. β-Lactam antibiotics are often inactivated by penicillinase, and chloramphenicol, tetracyclins and streptomycine exhibit a considerable number of undesired side effects in many cases (see Walter, Heilmeyer, Antibiotika Fibel (Antibiotics Primer), Georg Thieme Verlag, Stuttgart, 3rd edition, 1969, pages 248, 278–280 and 311–319).

It has now been found that a new antibiotic compound is obtained if the strain Streptomyces spec. WS 116 is grown in a nutrient medium and the compound is isolated from the nutrient medium.

The new antibiotic compound has a powerful antimicrobial action. It can be iron-free or iron-containing. Both forms can be successfully employed as an antibacterial agent. (The new antibiotic compound is referred to for brevity hereinafter as "BAY i 3265 Component A").

The new compound in the iron-free form may be characterised by the following properties:

(1) The elementary analysis C 43.8%; H 6.7%; N 14.1%; O 30.3%; S 4.1%.

It must be pointed out here that, in the case of higher-molecular natural substances, the margin of error of the elementary analysis can be greater than is generally customary, and an exact determination of the total molecular formula is therefore often not possible (R. B. Woodward, Angew, Chem. 69, pages 50–51 (1957)).

(2) The freeze-dried compound melts between 180° and 185° C. and decomposes on further warming.

(3) Ultraviolet absorption spectrum:

The UV spectrum was recorded for an aqueous solution of the compound (C=2.863 mg in 50 ml of $H_2O$). The spectra in acid (or basic) solution were measured on a solution which was prepared by the addition of 100 microliters of 1 N hydrochloric acid (or sodium hydroxide solution) to 3 ml of the above solution.

TABLE 1

Maxima (λ max) and extinctions $\left[E\frac{1\%}{cm}\right]$ of the compound

| | max [mμ] | $\left[E\frac{1\%}{cm}\right]$ |
|---|---|---|
| neutral | 267 | 103 |
| acid | 267 | 97.10 |
| basic | — | — |

(4) The IR absorption spectrum of the compound is represented in accompanying FIG. 1 (abscissa: wave number in $cm^{-1}$, ordinate: absorption).

When the substance is pressed into KBr pressed plates, the spectrum shows absorption bands at the following wavelengths (expressed in $cm^{-1}$):

TABLE 2

| Wavelengths of the IR absorption spectrum | |
|---|---|
| Wavelength in $cm^{-1}$ | Wavelength in $cm^{-1}$ |
| 3384 | 1210 |
| 2918 | 1160 |
| 1654 | 1090 |
| 1615 | 970 |
| 1540 | |
| 1457 | |
| 1415 | |
| 1390 | |
| 1300 | |
| 1240 | |

Figure 2:
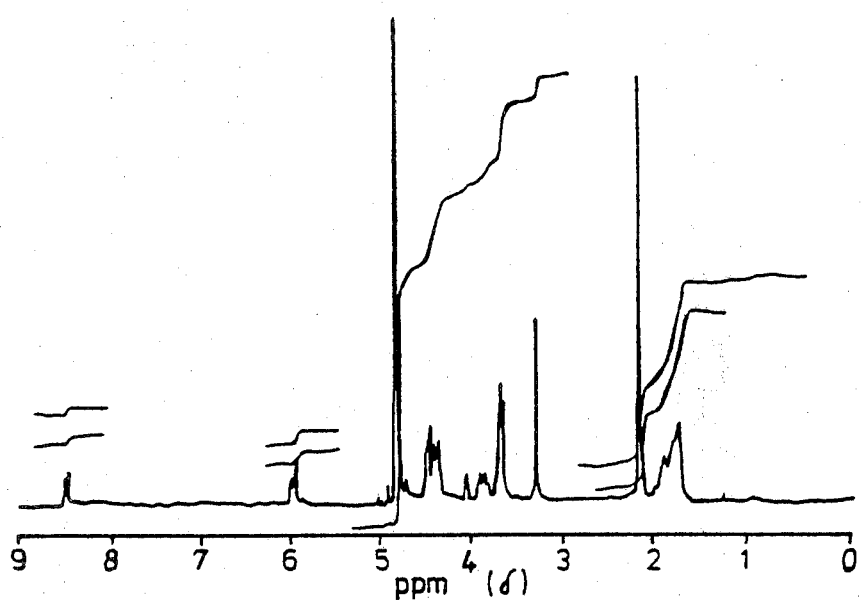

(5) the $^1H$ nuclear resonance spectrum gives the signal position in parts per million (ppm) and vibrations per second, according to accompanying FIG. 2. It was recorded for an aqueous solution of the compound, using the 3(Trimethylsilyl)propionic acid-d4 sodium salt as a standard (external), on a WH-360 spectrometer of Messrs. Bruker, at a field strength of 360 MHZ.

(6) The 13-C nuclear resonance spectrum was recorded on a WM-250 spectrometer of Messrs. Bruker, at a field strength of 62.71 MHZ, for an aqueous solution of the compound, the results being converted to correspond to dioxan as the external standard (shift position 67.400 ppm relative to tetramethylsilane=0).

Figure 3:
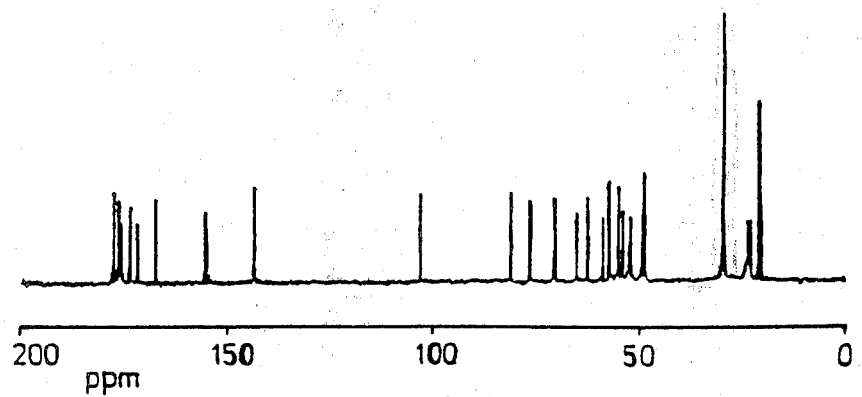

The 13-C nuclear resonance spectrum according to FIG. 3 shows the following signals, given in parts per million (ppm) and vibrations per second (HZ), in their relative intensities:

TABLE 3

Shift positions and intensities of the signals in the 13-C nuclear resonance spectrum relative to dioxan = 67.400 ppm (external)

| Signal NS | Relative intensity | Signal position (ppm) |
|---|---|---|
| 1 | 11.061 | 20.222 |
| 2 | 2.101 | 20.511 |
| 3 | 3.960 | 22.305 |
| 4 | 4.026 | 23.173 |
| 5 | 3.867 | 23.364 |
| 6 | 16.325 | 29.919 |
| 7 | 4.636 | 47.906 |
| 8 | 6.720 | 48.097 |
| 9 | 4.263 | 51.317 |
| 10 | 4.490 | 53.464 |
| 11 | 4.625 | 54.302 |
| 12 | 5.906 | 54.45 |
| 13 | 6.302 | 56.346 |

(7) The optical rotation value is $[\alpha]_D^{20}=-20.216$ (C=0.3941% in water).

(8) The compound has an unlimited solubility in water at pH 7, is slightly soluble in methanol, dimethylformamide and dimethylsulphoxide, and is sparingly soluble in chloroform, ether, ethyl acetate and petroleum ether.

By "slightly soluble" we mean a solubility of less than 10 g/l and by "sparingly soluble" we mean a solubility of less than 0,1 g/l.

(9) The compound is a colourless, amorphous solid, the aqueous solution of which has a neutral reaction.

(10) The $R_f$ values of the compound in the iron-free and iron-containing form, in comparison with other compounds in various mobile solvents, are given in Table 4.

(a) Instant thin layer chromatography plates silica gel 60 F 254 (Merck)
Coloration: 1. ninhydrin; 2. 5% $FeCl_3 \times 6H_2O$ in 0.5 N HCl Mobile solvent 1 (S 1): isobutanol/ethanol/ammonia=9/1/5
Mobile solvent 2 (S 2): isobutanol/ethanol/ammonia=4/1/5
10 cm length of run/charge 50 μg in distilled water TABLE 4a

| Substance | S1 | S2 |
|---|---|---|
| Neomycin sulphate | 0.01 | 0.16 |
| 2-Desoxystreptamine × 2 HCl | 0.03 | 0.19 |
| Sisomicine base | 0.14 | 0.42 |
| Compound according to the invention, iron-free | 0.02 | 0.26 |
| Compound according to the invention, iron-containing | 0 | 0.23 |

(b) Instant thin layer chromatograph plates cellulose F (Merck)
Coloration: 1. ninhydrin, 2. 5% FeCl$_3$×6H$_2$O in 0.5 N HCl
Mobile solvent 1 (S1): 1-butanol/glacial acetic acid/distilled water 4/1/5
Mobile solvent 2 (S2): 1-butanol/glacial acetic acid/distilled water 4/1/2
Mobile solvent 3 (S3): 1-propanol/pyridine/glacial acetic acid/distilled water 15/10/3/12
10 cm length of run/charge 50 g in distilled water.

TABLE 4b

| Substance | S1 | S2 | S3 |
|---|---|---|---|
| Neomycine sulphate | 0.06 | 0.06 | 0.06 |
| 2-Desoxystreptamine × 2 H$_2$O | 0.10 | 0.13 | 0.42 |
| Sisomicine base | 0.16 | 0.27 | 0.49 |
| Compound according to the invention, iron-free | 0.37 | 0.42 | 0.83 |
| Compound according to the invention, iron-containing | 0.14 | 0.25 | 0.74 |

(11) The new compound, in its iron-free form, can be made visible on the thin layer plate with FeCl$_3$*, alkaline potassium permanganate, iodine or ninhydrin, and in UV light at 254 or 280 nm by fluorescence extinction.
*The spray reagents were prepared according to the customary recipes (for example E. Stahl Dünnschicht-chromatographie (Thin Layer Chromatography), 2nd edition, Springer Verlag, Berlin).

(12) In the aminoacid analysis, when the hydrolysis is carried out in a closed flask for 24 hours at 110° C., the total hydrolysis of the compound with aqueous 57% strength hydriodic acid shows that the substance contains three units of ornithine, in addition to one unit of serine. Apart from these, only traces of other natural aminoacids were found.

By the preparation of derivatives and isolation of the hydrolysis products and the derivatives thereof, it was possible to elucidate the constitution of the compound BAYi 3265 Component A according to the invention.

According to the present invention there is therefore an antibiotic compound which, in the iron-free form, is of the formula

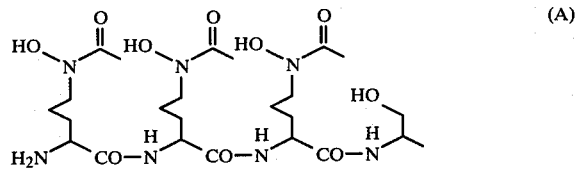

(A)

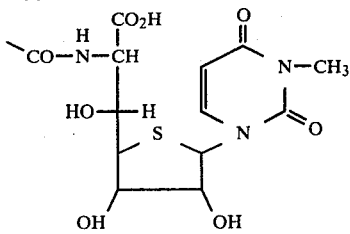

A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxyethanesulfonic, ethylenesulfonic, benzenesulfonic, halogenobenzenesulfonic, toluenesulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Racemate mixtures can be separated into the pure racemates in a known manner on the basis of the physicochemical differences of the constituents, for example by chromatography and/or fractional crystallization.

Pure racemates can be resolved according to known methods, for example by recrystallization from an optically active solvent, with the aid of micro-organisms or by reaction with an optically active acid or base which forms salts with the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end product in the form of pure racemates or optical antipodes by employing starting substances, containing one or more asymmetrical C atoms, in the form of the pure racemates or optical antipodes.

The compound of the present invention may be characterised in practice by just some of the above-mentioned properties.

According to the present invention there is therefore, provided an iron-free or iron-containing antibiotic compound, with a melting point of 180° to 185° C. and an optical rotation $[\alpha]_D^{20} = -20.216$ (C=0.3941% in water) as the iron-free substance, which is readily soluble in water at pH 7, slightly soluble in methanol, dimethylformamide and dimethylsulphoxide and sparingly soluble in chloroform, ether, ethyl acetate and petroleum ether, has a maximum at 267 m$\mu$ in the UV spectrum in water (neutral and acid), and, as a KBr pressed plate, has absorption maximum at 3348, 2918, 1654, 1615, 1540, 1457, 1415, 1390, 1300, 1240, 1210, 1160, 1090 and 970 cm$^{-1}$ in the infrared range, and releases ornithine and serine in the ratio 3:1 on acid hydrolysis, and, preferably, with a 1 H-NMR spectrum according to accompanying FIG. 2, with a 13C-NMR spectrum according to accompanying FIG. 3 and with a maximum of 267 m$\mu$ in the UV spectrum.

The compound according to the present invention is produced by the submerse culture of a Streptomycetes strain in suitable nutrient solutions and under suitable physical conditions. It is separated off from the culture solution by extraction or by absorption, and is concentrated by further suitable methods.

According to the present invention there is therefore provided a process for the production of the antibiotic compound of the present invention, in which Streptomyes spec. WS 116 (DSM 1692) is grown, under submerse, aerobic conditions in a nutrient medium containing assimilable sources of carbon, nitrogen and one or more mineral salts, particularly an iron salt or salts, at a temperature of from 15° to 35° C., and the compound formed is isolated from the fermentation liquid.

The new strain Streptomyces spec. WS 116 from the order of the Actinomycetales, Streptomycetaceae family, genus Streptomyces, or variants and mutants originating from this strain, can be employed for the preparation process. This strain was isolated from a marine soil sediment sample of the Ibero-Canary Sea. It was deposited in the Deutsche Sammlung für Mikroorganismen (German Collection of Microorganisms), Göttingen on 7.12.1979, under the number DSM 1692. It has the following characteristics:

(a). The spores are ellipsoidal. They have the dimensions 0.4–0.7×0.7–1.2$\mu$ and a smooth surface.

(b). The colour of the sporulated mycelium is chalk-white in the beginning and yellowish in the mature state (Griseus type).

(c). The spore chains are straight or wavy (Rectus-Flexibilis type) and monopodially branched.

(d). No black-brown pigment was formed on the peptone iron agar and on the tyrosine agar. The strain is not chromogenous.

The summarised determining characteristics identify the strain WS-116 as belonging to the species *Streptomyces griseus* Waksman et Henrici.

Nutrient media which contain the customary carbon and nitrogen sources and the necessary salts are used for the process for the preparation of the compound according to the invention.

The following can be used as the carbon source: carbohydrates, particularly polysaccharides (such as starch or dextrins), disaccharides, (such as maltose or cane sugar), monosaccharides (such as glucose or xylose), sugar alcohols (such as mannitol or glycerol), carboxylic acids (such as citric acid, malic acid or acetic acid), or mixtures thereof, and, in addition, also naturally occurring mixtures, such as malt extract. Surprisingly, the highest active compound yields were obtained with carboxylic acids, particularly with citric acid, as the main C source.

The customary nitrogen sources, such as proteins, protein hydrolysates, aminoacids (such as glutamic acid, aspartic acid, arginine, lysine, ornithine or serine), and, in addition, nucleoside bases (such as cytosine or uracil), ammonium salts, nitrates, naturally occurring complex substances (such as peptones, corn-steep liquor, soya bean flour, meat extracts or yeast extracts) and suitable mixtures of these substances can be used as the nitrogen source. Particularly high active compound yields are obtained if, in addition to the customary complex N sources, L-ornithine and L-serine are added, in sterile-filtered form, in the weight ratio 3:1, for example 0.3% and 0.1% by weight, to the medium.

Mineral salts, for example phosphates, sulphates, carbonates, nitrates or chlorides of sodium, potassium, calcium, magnesium, iron, zinc, copper, molybdenum, cobalt, nickel and manganese, are necessary, as auxiliaries, in the nutrient medium. The presence of about 0.01% by weight of FeCl$_3$ proved to be significant. Some of the mineral salts, also the FeCl$_3$, are contained as constituents, in the required concentrations, in the above-mentioned carbon or nitrogen sources or in the water used.

Furthermore, anti-foam agents of the most diverse type, such as soya oil, polyols or silicones, can also be used as auxiliaries.

Water may be mentioned as the most important diluent for the nutrient media.

It has been found to be particularly effective if the fermentation is carried out either in a nutrient solution which contains citric acid as the main carbon source, several naturally occurring complex nitrogen sources and the aminoacids L-ornithine and L-serine, or in a completely synthetic nutrient solution which, in addition to mineral salts, contains citric acid as the carbon source and L-arginine as the only nitrogen source.

The yield of the process of the invention may be increased if a mixture of citric acid, L-arginine and salts is further fed to the nutrient solution at such a rate that a constant pH value of about 7.5 is maintained.

The preparation process is carried out under aerobic or microaerophilic conditions; the culture can be carried out according to customary methods, for example using shake cultures or aerated fermenter cultures in the customary batch or fedbatch process. The percentage ratios (percentages by weight in each case) of the nutrient solution constituents can vary within wide ranges, and, in general, the carbon sources make up to 0.5 to 8%, preferably 0.6 to 6% in total, and the nitrogen sources make up 0.05 to 4%, preferably 0.5 to 2% in total; the salts are present in customary concentrations, preferably in the range between 0.001 and 0.5% by weight. The anti-foam agents are present in 0 to 1% concentration. The temperatures used for sterilisation are 100° to 140° C., preferably 120° to 130° C., and sensitive substances, such as aminoacids, are sterilised by filtration.

The pH values of the growing cultures are between 5 and 10, preferably between 6 and 9.5. The growth temperature can be between 15° and 35° C., preferably between 20° and 30° C. It has been found that the quantity of the antibiotic being concentrated in the culture broth reaches its maximum, in general, about 1 to 10, preferably about 2 to 6 days after the beginning of growing. The end point of the fermentation is determined with the aid of biological tests (action against *E. coli* in a customary agar diffusion test).

The compound according to the invention is generally isolated from the culture filtrate by extraction with mixtures of phenol/chloroform, or by adsorption onto active charcoal or onto suitable resins. The compound according to the invention is advantageously bound to non-specific adsorption resins based on polystyrene (for example "Amberlite" XAD—Trade Mark of Messrs. Rohm & Haas or "Lewatit" OC 1031—Trade Mark of Messrs. Bayer).

It has surprisingly been found that the compound according to the invention is particularly firmly bound by non-specific adsorption resins if, before the adsorption process, iron salts, particularly iron chloride, are added, generally in concentrations of 0.05 to 0.2, preferably approximately 0.1, g/liter of culture broth. The adsorption is carried out in the pH range 3-9, particularly in the range 5-7. The desorption of the compound according to the invention from such resins is carried out fractionally with mixtures of water and organic solvents, particularly water/methanol. The active fractions are combined, concentrated to a small volume and lyophilised. A 0.5-3% strength crude product is obtained, which contains the compound according to the invention, in addition to other substances.

Starting from this crude product, the further concentration of the compound according to the invention can be carried out by a combination of anion exchange chromatography (for example DEAE-"Sephadex" A 25—Trade Mark of Messrs. Pharmacia) or cation exchange chromatography (for example SP- or CM-"Sephadex" C 25—Trade Mark of Messrs. Pharmacia). A 30-50% strength preparation is obtained thereby, since accompanying peptides are not separated off. Separating off these peptides and thus preparing the pure compound is effected by adsorption chromatography or partition chromatography of the approximately 30 to 50% strength compound over silica gel in the system isobutanol/ethanol/25% concentrated ammonia=9/1/5 (parts by volume).

However, this separation process is associated with substance losses.

The separation is achieved in a substantially simpler manner by means of afffinity chromatography over a cation exchanger in a $Fe^{3+}$-containing column. For this purpose, a cation exchanger based on polystyrene resin or on acrylic resin (for example "Dowex" 50 WX 4—Trade Mark of Messrs. Dow Chemical), or based on polydextrane (for example "Sephadex" C 25—Trade Mark of Messrs. Pharmacia) can be converted, using $FeCl_3$ solution, into the $Fe^{3+}$ form. The solution of the crude product is now introduced onto the resin in the $Fe^{3+}$ form, and is then rinsed with water. The column is then eluted with a buffer of high ionic strength, for example 0.2 M $NaH_2PO_4$/0.3 M NaCl. This buffer elutes the bulk of the inactive accompanying peptides. The active substances are then eluted from the column, using the same buffer but with the addition of 0.05 M ethylenediaminetetraacetic acid or another iron complex-forming agent (for example citrate). The active fractions are combined and are introduced over a column with a non-specific adsorption resin (for example "Lewatit" OC 1031—Trade Mark of Messrs. Bayer), the active substances being bound. The column is eluted with methanol, and the runnings are concentrated and lyophilised.

The compound according to the invention may be obtained in pure form by means of partition chromatography on "Sephadex" G 25 in n-BuOH/iso BuOH/0.2 M $(NH_4)_2SO_4=2/1/1$.

The purification of the product according to the invention may be further carried out by simple chromatography of the active compound mixture on a CM-cellulose column in the $H^+$ form, using distilled water without any additives. The eluate, collected in fractions, is lyophilised.

The good antimicrobial (e.g. antibacterial) activity of the compound according to the invention is demonstrated by in vitro and in vivo tests.

In vitro activity against enterobacteriaceae, for example *E. coli* 14 and *E. coli* C 165, are found in the agar dilution test according to the internationally customary test (American National Committee for Clinical Laboratory Standards=NCCLS).

For the white mouse, an $ED_{100}$ (complete cure) is found in vivo, at 3 mg of antibiotic/kg of body weight, on infection with *E. coli* Neumann; therapy: application once, 30 minutes after infection, subcutaneously.

As stated above, the invention also relates to the use in medicine as antimicrobial agents of the compounds of the invention.

The present invention provides a pharmaceutical composition containing as active ingredient a compound of the invention in admixture with an inert pharmaceutical carrier, e.g. a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a)

fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencasulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

In addition to a compound of the invention, the pharmaceutical compositions and medicaments according to the invention can also contain other pharmaceutically active compounds.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets)

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally.

In general it has proved advantageous to administer amounts of from 0.1–100 mg/kg of body weight per day to achieve effective results. The preferred dose rate is 2–50 mg/kg. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The in vivo and in vitro activity of the compounds of the present invention is further illustrated by the following Examples A and B.

EXAMPLE A

BAYi 3265 Component A (iron-containing)

| Germ | MIC in/μg/ml |
| --- | --- |
| Escherichia coli F14 | 0.1 |
| Escherichia coli 183/58 | 0.1 |
| Escherichia coli 14 | 0.1 |

The determination of the minimum inhibitory concentration (MIC) was effected with an inoculator in the agar dilution process, with a sowing density of $10^4$ per inoculation point. The MIC was the concentration at which no bacteria colonies grew.

EXAMPLE B

BAYi 3265 component A animal test (mice)

| Infecting germ | $ED_{100}$ after intraperitoneal infection and subcutaneous treatment in mg/kg |
| --- | --- |
| E. coli Neumann | 0.5 |
| E. coli 205 Kn | 0.1 |
| Klebsiella pneumoniae 63 | 0.2 |
| Staphylococcus aureus 133 | 0.6 |

The animals were infected with a quantity of bacteria, which quantity led to the death of the control animals within 24 hours. The $ED_{100}$ was the dose which allowed all infected and treated animals to survive.

The following Examples illustrate processes for the production of the compound of the present invention.

EXAMPLE 1

(a) The nutrient solution in which the production strain Streptomyces spec. WS 116 was cultivated in the precultures was composed of 1% by weight of glucose, 1.3% of yeast extract, 0.05% of polyol and tapwater. The pH was adjusted to 7.0 before the sterilisation. 4×1000 ml Erlenmeyer flasks, each of which contained 150 ml of this nutrient solution, were inoculated with the production strain and were incubated for 4 days at 28° C. on a rotary shaking machine at 220 revolutions/minute. A second preculture in a laboratory fermenter, which contained 20 liters of the above mentioned nutrient solution, was inoculated with these precultures and incubated for 2 days at 200 revolutions/minute, 10 liters of air/minute at 28° C. 20 liters of this culture were used for inoculating a production fermenter which contained 600 liters of nutrient solution with the following composition: 0.7% by weight of citric acid, 0.8% of yeast extract, 0.2% of de-fatted soya bean flour, 0.2% of corn-steep liquor and 0.05% of silicone in tap water. The pH of this nutrient solution was adjusted, before the sterilisation to 6.4 using potassium hydroxide solution. The incubation of the production culture was effected over 2 to 4 days at 26° C. and at a stirring rate of 50 revolutions/minute and an aeration of only 90 liters of air/minute. The fermentation was stopped at the optimum antibiotic inhibitory activity of the culture.

(b) 2×150 ml of the preculture were grown as indicated in Example 1(a). These precultures were used for inoculating a 10 liter production fermenter, the nutrient solution of which, prepared in tap water, contained the following composition: 0.7% by weight of citric acid, 0.8% by weight of yeast extract, 0.2% by weight of de-fatted soya bean flour, 0.2% by weight of corn-steep liquor, 0.3% by weight of L-ornithine, 0.1% by weight of L-serine and 0.05% by weight of silicone.

All constituents except ornithine and serine were sterilised, as customary, in the culture vessel. A pH value of 6.4 was established before the sterilisation. Ornithine and serine, dissolved in distilled $H_2O$, were added to the mixture in a sterile-filtered form.

The incubation of the production culture was effected over 2 to 4 days at 26°, at a stirring rate of 200 revolutions/minute and an aeration of only 1.5 liters of air/minute. The fermentation was stopped at the optimum antibiotic inhibitory activity of the supernatant culture liquor.

EXAMPLE 2

4000 liters of culture broth (pH=9.06) were adjusted to pH 6.2 using 50 liters of 1:1 dilute HCl. 400 g of $FeCl_3.6H_2O$ were added to the broth, the latter was stirred and 25 liters of dilute NaOH were then added, whilst stirring, until the pH was 7. The mixture was then separated, at 200 to 250 liters/hour, in a Westphalia separator. The supernatant liquor was introduced through a 30×70 cm high column filled with "Lewatit" OC 1031 (Trade Mark of a non-specific adsorption resin of Bayer AG), and the permeate was conducted away as waste since it was inactive. The column was washed with 1000 liters of deionised water; the wash water was inactive and was discarded. The column was now washed with 1000 liters of 15% methanol, and this inactive wash liquor was also discarded. The activity was now eluted from the column using 50% methanol, and 100 liter fractions were collected. The active eluates 2 and 3 were combined, concentrated to approximately 20 liters in a thin layer evaporator and then lyophilized. 342 g of crude product, of the compound according to the invention, with a content of approximately 2.5% (component A according to the invention and another antibiotic compound—component B) were obtained.

EXAMPLE 3

The above crude substance was dissolved in 6 liters of $H_2O$ and 25 ml of 50% strength $FeCl_3$ solution were added to the solution, whilst stirring. The precipitate which formed was centrifuged off after the mixture had been stirred for 15 minutes (Hettich Rota Magna centrifuge, 1.5 liter beaker, 30 min, 4000 rpm). The supernatant liquor was introduced, under the influence of gravity, over an 8×45 cm high column filled with SP-"Sephadex" C 25 $Fe^{3+}$. The flow rate was 4 liters per hour. The black coloured column was rinsed with 5 liters of distilled $H_2O$, followed by 10 liters of 0.2 M $NaH_2PO_4$/0.3 M NaCl buffer. The permeate and wash liquor contained less than 5% of the antibiotic activity introduced. The column which was now only pale brown coloured was not eluted with 0.2 M $NaH_2PO_4$/0.3 M NaCl/0.05 M ethylenediaminetetra-acetic acid (flow rate 2 to 3 l/hr), and the column eluate was collected fractionally in 500 ml portions. The active fractions 6 to 14 were combined and were introduced over a 5×40 column filled with Lewatit OC 1031. The flow rate was 3 l/hr. The column was then washed with distilled water until, using $AgNO_3$ no $Cl^-$ could be detected in the column eluate (approximately 6 liters, flow rate 5 l/hr). The column was then eluted with 3 liters of 90% methanol, which were collected in a batch, concentrated and lyophilised. Yield: 6.74 g, 82.6%, of component A and B.

EXAMPLE 4

Half the yield from Example 2—3.37 g were dissolved in 100 ml of distilled H₂O. The conductivity was 210 μS.

The solution was introduced onto a 5×30 cm column filled with CM-cellulose in the H⁺ form (CM-cellulose C 52, Messrs, Whatmann). The column was developed with distilled water, at a flow rate of 840 ml/hr. The eluate was fractionated on the basis of the refraction curve, conductivity curve and extration curve. First runnings (inactive) of 930 mg were obtained.

| Fraction 1 | 427 mg |
|---|---|
| Fraction 2 | 674 mg |
| Fraction 3 | 363 mg |
| Fraction 4–6 | 475 mg |
| Fraction 7 | 253 mg |
| Fraction 8 | 96 mg |

Fraction 1 was the compound according to the invention, Bayi 3265, component A.

What is claimed is:

1. An antibiotic compound which, in the iron-free form, is of the formula

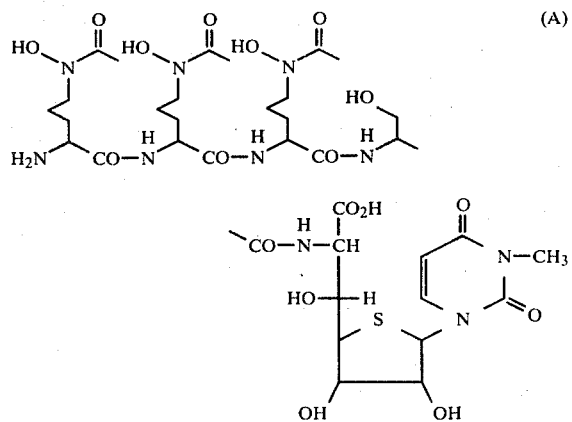

2. An iron-free or iron-containing antibiotic compound, according to claim 1 with a melting point of 180° to 185° C. and an optical rotation $[\alpha]_D^{20} = -20.216$ (C=0.3941% in water) as the iron-free substance, which is readily soluble in water at pH 7, slightly soluble in methanol, dimethylformamide and dimethylsulphoxide, and sparingly soluble in chloroform, ether, ethyl acetate and petroleum ether, has a maximum at 267 mμ in the UV spectrum in water (neutral and acid), and, as a KBr pressed plate, has absorption maximum at 3348, 2918, 1654, 1615, 1540, 1457, 1415, 1390, 1300, 1240, 1210, 1160, 1090 and 970 cm⁻¹ in the infrared range and releases ornithine and releases ornithine and serine in the ratio 3:1 on acid hydrolysis.

3. An antibiotic compound according to claim 1 or 2, characterized by the 1 H-NMR spectrum according to accompanying FIG. 2, by the 13C-NMR spectrum according to accompanying FIG. 3 and by a maximum at 267 mμ in the UV spectrum.

4. A pharmaceutical composition containing as an active ingredient an antibacterially effective amount of a compound according to claim 1 in admixture with an inert pharmaceutical carrier.

5. A pharmaceutical composition of claim 4 in the form of a sterile or physiologically isotonic aqueous solution.

6. A composition according to claim 4 or 5 containing from 0.5 to 95% by weight of the said active ingredient.

7. A medicament in a dosage unit form, containing as an active ingredient an antibacterially effective amount of a compound according to claim 1 in admixture with an inert pharmaceutical carrier.

8. A method of combating bacterial infections in warm-blooded animals which comprises administering to the animals antibacterially effective amount of an active compound according to claim 1 either alone or in admixture with a diluent or in the form of a medicament.

9. A method according to claim 8 in which the active compound is administered in an amount of 0.1 to 100 mg per kg body weight per day.

10. A medicament of claim 7 in the form of tablets, pills, dragees, capsules, ampules, or suppositories.

* * * * *

UNITED STATES PATENT AND TRADEMARK OFFICE
CERTIFICATE OF CORRECTION

PATENT NO. : 4,416,870

DATED : November 22, 1983

INVENTOR(S) : Karl G. Metzger et al

It is certified that error appears in the above-identified patent and that said Letters Patent is hereby corrected as shown below:

Col. 2, line 47  Insert deleted chart:

| Signal NS | Relative intensity | Signal postion (ppm) |
|---|---|---|
| 14 | 4.260 | 58.317 |
| 15 | 5.171 | 61.993 |
| 16 | 4.332 | 64.581 |
| 17 | 5.260 | 70.022 |
| 18 | 5.100 | 75.962 |
| 19 | 5.436 | 80.536 |
| 20 | 5.437 | 102.328 |
| 21 | 5.790 | 142.604 |
| 22 | 4.421 | 153.765 |
| 23 | 5.004 | 166.249 |
| 24 | 3.694 | 170.322 |
| 25 | 4.663 | 171.837 |
| 26 | 3.740 | 174.028 |
| 27 | 3.837 | 174.395 |
| 28 | 5.046 | 174.778 |
| 29 | 2.662 | 174.925 |
| 30 | 5.686 | 175.792 -- |

Col. 5, line 31  Delete "Streptomyes" and insert --Streptomyces--

Col. 7, line 48  Delete "afffinity" and insert --affinity--

UNITED STATES PATENT AND TRADEMARK OFFICE
CERTIFICATE OF CORRECTION

PATENT NO. : 4,416,870

DATED : November 22, 1983

INVENTOR(S) : Karl G. Metzger et al

It is certified that error appears in the above-identified patent and that said Letters Patent is hereby corrected as shown below:

Col. 12, line 56  Delete "not" and insert --now--

Col. 13, line 12  Delete "930" and insert --980--

Col. 14, line 13  Delete "and releases ornithine" second occurrence.

Signed and Sealed this

Ninth Day of October 1984

[SEAL]

Attest:

GERALD J. MOSSINGHOFF

Attesting Officer

Commissioner of Patents and Trademarks